United States Patent

Merz et al.

(10) Patent No.: US 9,513,247 B2
(45) Date of Patent: *Dec. 6, 2016

(54) ELECTROCHEMICAL SENSOR

(71) Applicant: ams International AG, Rapperswil-Jona (CH)

(72) Inventors: Matthias Merz, Leuven (BE); Dimitri Soccol, Rotselaar (BE)

(73) Assignee: AMS INTERNATIONAL AG, Rapperswil-Jona (CH)

( * ) Notice: Subject to any disclaimer, the term of this patent is extended or adjusted under 35 U.S.C. 154(b) by 259 days.

This patent is subject to a terminal disclaimer.

(21) Appl. No.: 14/192,648

(22) Filed: Feb. 27, 2014

(65) Prior Publication Data

US 2015/0241375 A1  Aug. 27, 2015

(51) Int. Cl.
| | | |
|---|---|---|
| G01N 27/30 | (2006.01) | |
| G01N 27/404 | (2006.01) | |
| G01N 27/407 | (2006.01) | |
| G01N 33/00 | (2006.01) | |

(52) U.S. Cl.
CPC .......... *G01N 27/30* (2013.01); *G01N 27/4045* (2013.01); *G01N 27/407* (2013.01); *G01N 33/004* (2013.01); *Y10T 29/49117* (2015.01)

(58) Field of Classification Search
CPC .. G01N 27/30; H05K 13/0023; H05K 13/00; H04N 5/374; H01L 21/8238
See application file for complete search history.

(56) References Cited

U.S. PATENT DOCUMENTS

| | | | |
|---|---|---|---|
| 3,616,416 A | 10/1971 | Linenberg et al. | |
| 4,913,792 A | 4/1990 | Nagata et al. | |
| 5,215,643 A | 6/1993 | Kusanagi et al. | |
| 6,376,124 B1 * | 4/2002 | Dodgson | B01J 19/0093 |
| | | | 429/127 |
| 8,852,513 B1 | 10/2014 | Speer et al. | |
| 2003/0121781 A1 | 7/2003 | Prohaska et al. | |
| 2004/0026246 A1 * | 2/2004 | Chapples | G01N 27/4074 |
| | | | 204/424 |
| 2004/0026268 A1 | 2/2004 | Maki et al. | |
| 2008/0128285 A1 | 6/2008 | Moon et al. | |
| 2010/0133120 A1 | 6/2010 | Varney et al. | |
| 2011/0226619 A1 | 9/2011 | Eckhardt et al. | |
| 2011/0253534 A1 | 10/2011 | Eckhardt et al. | |

(Continued)

FOREIGN PATENT DOCUMENTS

| | | |
|---|---|---|
| DE | 10323858 A1 | 12/2004 |
| EP | 0125807 A2 | 11/1984 |

(Continued)

OTHER PUBLICATIONS

Gardner et al., CMOS Interfacing for Integrated Gas Sensors: A Review, (IEEE Sensors Journal, vol. 10, No. 12, Dec. 2010).

(Continued)

*Primary Examiner* — Jennifer Dieterle
(74) *Attorney, Agent, or Firm* — McDermott Will & Emery LLP (57) ABSTRACT

An electrochemical sensor for sensing a target substance is disclosed. In one example, the sensor discloses an electrolyte matrix, wherein the matrix reposits an electrolyte; a working electrode coupled to the electrolyte matrix at a first location; a counter electrode coupled to the electrolyte matrix at a second location; an electrical circuit, coupled to the working electrode and the counter electrode, and capable of generating an output signal in response to an electrical current which flows between the working electrode and the counter electrode in response to a presence of the target substance.

16 Claims, 12 Drawing Sheets

(56) References Cited

U.S. PATENT DOCUMENTS

| | | |
|---|---|---|
| 2012/0036921 A1 | 2/2012 | De Coulon et al. |
| 2012/0098075 A1 | 4/2012 | Lamagna et al. |
| 2013/0091924 A1* | 4/2013 | Scheffler .............. G01N 33/497 73/23.3 |
| 2013/0144131 A1 | 6/2013 | Wang et al. |

FOREIGN PATENT DOCUMENTS

| | | |
|---|---|---|
| EP | 0432757 A2 | 6/1991 |
| EP | 0514873 A1 | 11/1992 |
| EP | 0625704 A2 | 11/1994 |
| EP | 13152411.8 | 1/2013 |

OTHER PUBLICATIONS

Wollenstein et al., "Material Properties and the influence of metallic catalysts at the surface of highly dense SnO2 films" Sensors and Actuators B, vol. 70 (2000), pp. 196-202.

Wollenstein et al., "Preparation, morphology and gas-sensing behavior of Cr2-xTixO3+z thin-films on standard silicon wafers" IEEE Sens. J., vol. 2 (2002), pp. 403-408.

Microsens; "Microsens Amperometric Sensor"; Sensor Description, retrieved from the internet Feb. 25, 2014 http://www.microsens.ch/products/pdf/Amperometric_Sensor.pdf; 2 pages.

Draeger; "XXS CO Sensor Specifications"; retrieved from the internet Feb. 25, 2014 http://www.draeger.com/sites/assets/PublishingImages/Products/cin_draegersensor_xxs/Master/9094331_Sensoren_PI_EN_111113_fin.pdf ; 4 pages.

Alphasense Limited; "Alphasense Application Note AAN 105-3 Desigining a Potentiostatic Circuit"; Great Notley, Essex, UK; 5 pages (Mar. 2009).

DropSens; "Customised SPEs"; retreived from the internet Feb. 25, 2014 http://www.dropsens.com/en/pdfs_productos/new_brochures/customised_spes.pdf; 1 page.

Underwriters Laboratories Inc; "UL2034, Single and Multiple Station Carbon Monoxide Alarms—Table of Contents"; 14 pages (Feb. 20, 2009).

DIN EN 50291-1 (VDE 0400-34-1); First Pages; 14 pages w/translation) (Nov. 2009).

Boutet et al., "Low power CMOS potentiostat for three electrodes amperometric chemical sensor", Faible Tension Faible Consommation (FTFC), 2011, IEEE, pp. 15-18, May 30, 2011.

Currie et al., "Micromachined Thin Film Solid State Electrochemical CO2, NO 2, and SO2 Gas Sensors" Sensors and Actuators B 59, pp. 235-241, 1999.

Dubbe, A. "Fundamentals of solid state ionic micro gas sensors", Sensors and Actuators,vol. 88, No. 2, pp. 138-148, Jan. 15, 2003.

Tan et al., "A 1.8V 11 W CMOS Smart Humidity Sensor for RFID Sensing Application" IEEE Asian Solid State Circuits Conference, Nov. 14-16, 2011, Jeju, Korea, pp. 105-108.

UL, "Carbon Monoxide Alarm Considerations for Code Authorities", The Code Authority newsletter, Issue 3, 2009.

Wollenstein et al., "A Novel Single Chip Thin Film Metal Oxide Array", Sensors and Actuators B 93, pp. 350-355, 2003.

Yamazaki et al., "Design and Fabrication of Complementary Metal-Oxide-Semiconductor Sensor Chip for Electrochemical Measurement", Japanese Journal of applied Physics, vol. 49, No. 4, p. 04DL11, Apr. 1, 2010.

Extended European Search Report for Application No. 13152411.8, dated Apr. 17, 2013,10 pages.

* cited by examiner

ELECTROCHEMICAL SENSOR

CROSS-REFERENCE TO RELATED OR CO-PENDING APPLICATIONS

This application may relate to and incorporates by reference U.S. patent application Ser. No. 14/159,036, entitled "Electrochemical Sensor Device", filed on 7 Feb. 2014, now issued as U.S. Pat. No. 9,395,318, by Merz et al. This application is assigned to ams International AG, Switzerland.

BACKGROUND

Brief Background Introduction

This specification relates generally to electrochemical sensors.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Multiple example embodiments of an electrochemical sensor are provided forthwith. Electrochemical sensors detect target substances and in response generate an electrical signal. The example embodiments to follow are for electrochemical sensor's designed to sense a target gas, however the teaching provided applies equally to sensing target liquids, molecules, solids, chemical elements, and the like. In one example embodiment the electrochemical sensor is used for monitoring a carbon compound such as carbon monoxide (CO) in a residential or a public building.

The electrochemical sensor includes an electrochemical cell portion and a potentiostat circuit. The electrochemical cell and the potentiostat circuit are coupled by a working electrode, a counter electrode and, depending on the required accuracy of the electrochemical cell, a reference electrode. These electrodes are coupled together by an electrolyte. In one example embodiment all electrodes+electrolyte=electrochemical cell.

The working electrode responds to a target gas by either oxidizing or reducing the gas and thereby creating a current flow that is proportional to the gas's concentration. This current is supplied to the electrochemical cell through the counter electrode.

The working electrode potential is maintained at the same potential as the reference electrode potential for unbiased electrochemical sensors, or with an offset potential for sensors that require biasing.

The counter electrode completes a circuit with the working electrode, and reduces a chemical species (e.g. oxygen) if the working electrode is oxidizing, or oxidizes a chemical species if the working electrode is reducing the target gas. The potential of the counter electrode is allowed to float, sometimes changing as the gas concentration increases. If a reference electrode is included, the potential on the counter electrode is not important, so long as the potentiostat circuit can provide sufficient voltage and current to maintain the working electrode at the same potential as the reference electrode.

The counter electrode is controlled by the potentiostat circuit such that the potential of the working electrode with respect to the potential of the reference electrode is kept constant. In case of two electrodes the counter electrode is controlled such that voltage between working electrode and counter electrode are kept constant.

The electrochemical cell includes an opening through which the gas molecules enter and subsequently diffuse into the electrolyte and to the electrodes where they are reduced or oxidized by the voltage applied between the electrodes. In case of one example embodiment of an electrochemical CO sensor the following reactions take place at the electrodes:

At sensing (working) electrode: $CO + H_2O \rightarrow CO_2 + 2H^+ + 2e^-$

At counter electrode: $\tfrac{1}{2}O_2 + 2H^+ + 2e^- \rightarrow H_2O$

Overall reaction is: $CO + \tfrac{1}{2}O_2 \rightarrow CO_2$

Three processes governing an equilibrium situation in one example embodiment of the electrochemical cell are:

Absorption of the target chemical at the electrolyte interface;

Transport of [CO] and [$O_2$] by diffusion; and

Chemical molecules adsorbed at the electrode surface.

This chemical reaction generates an electric current which is proportional to a number of reacting gas molecules entering the opening and thus the concentration of the gas can be calculated. The potentiostat controls the counter and measures the reference electrode potentials, measures the cell's currents and presents a read-out. Current within the potentiostat is limited by diffusion of CO molecules towards the electrodes. Below is an equation that allows for estimating the maximum current as a function of gas pressure:

$$i_l = \frac{nFAD_{CO}}{\delta} \frac{p_{CO}}{k_H - p_{CO}} c_{solvent}$$

Where: "n" is the number of electrons involved in the reaction, F Faraday's constant, A the electrode surface area, $D_{CO}$ the diffusion constant of CO in the electrolyte, $c_{CO}$ the concentration of CO molecules at the air-electrolyte interface and $\delta$ the thickness of the electrolyte. $D_{CO}$, $k_H$ and $c_{solvent}$ are material constants.

In one example embodiment, the electrochemical cell and potentiostat are fabricated using CMOS processes. Using CMOS technology, currents of about 15 pA can be resolved. In an example where a minimal required sensing resolution is 5 ppm CO and entering the electrolytes are water and an ionic liquid (e.g. Bmim or $NTf_2$), a minimal electrode surface area form factor (i.e. A(electrode)/δ(electrolyte)) for a 10 μm thick electrolyte is 0.16 to 1.1 $mm^2$. Further form factor downscaling can be achieved by decreasing the electrolyte thickness.

By using CMOS processes to fabricate the electrochemical sensor, both the electrochemical cell and potentiostat can be co-integrated within a single silicon die. This makes the electrochemical sensor very compact such that such electrochemical sensors can be ubiquitously incorporated into mobile devices such as cell phones and automotive vehicles. Such a compact form factor also decreases the risk of noise pick-up. While various example embodiments are presented below, features and manufacturing techniques of these example embodiments may be shared.

Figure 1A:
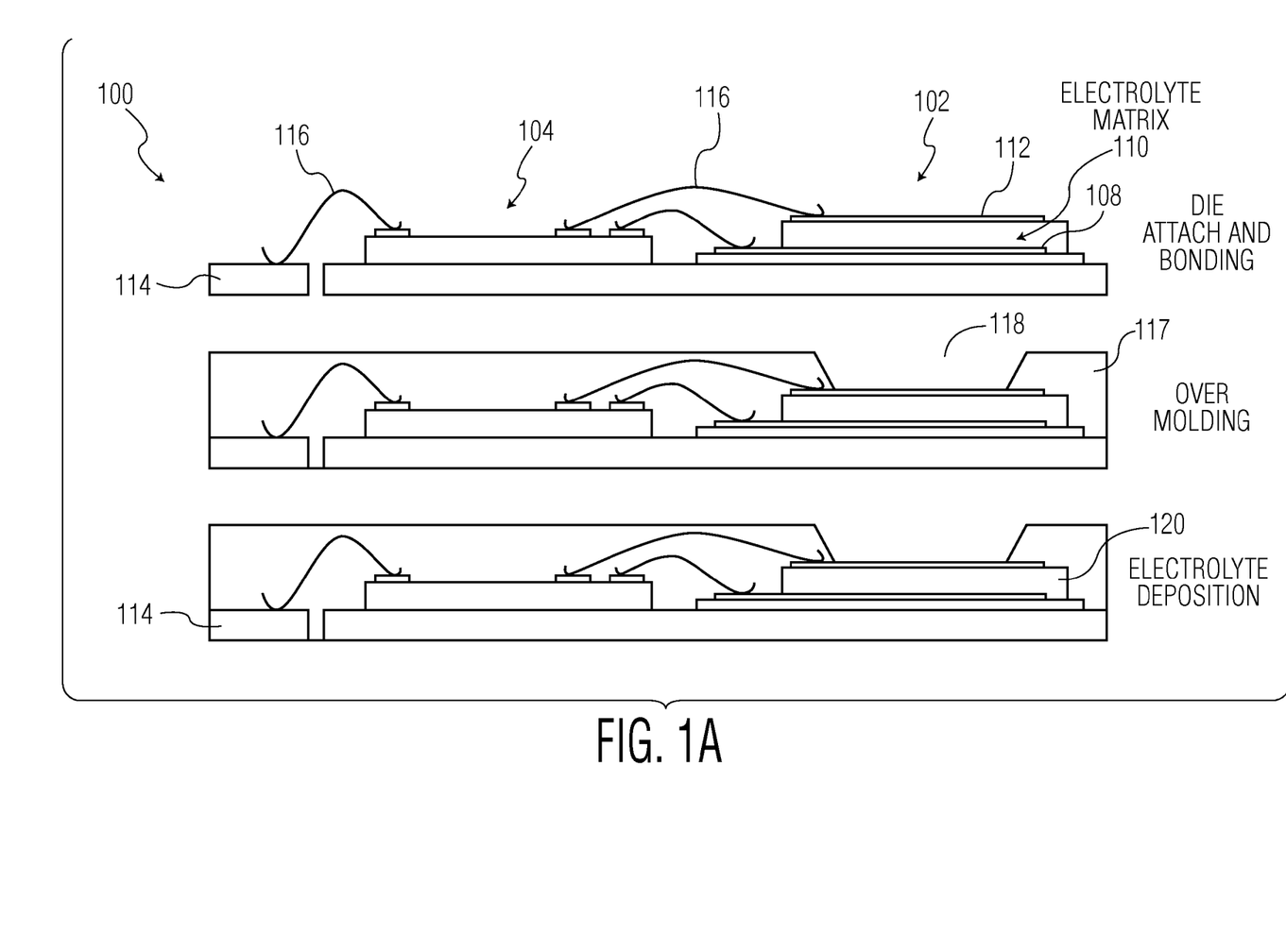
FIGS. 1A and 1B show one example of a first electrochemical sensor.
Figure 1B:
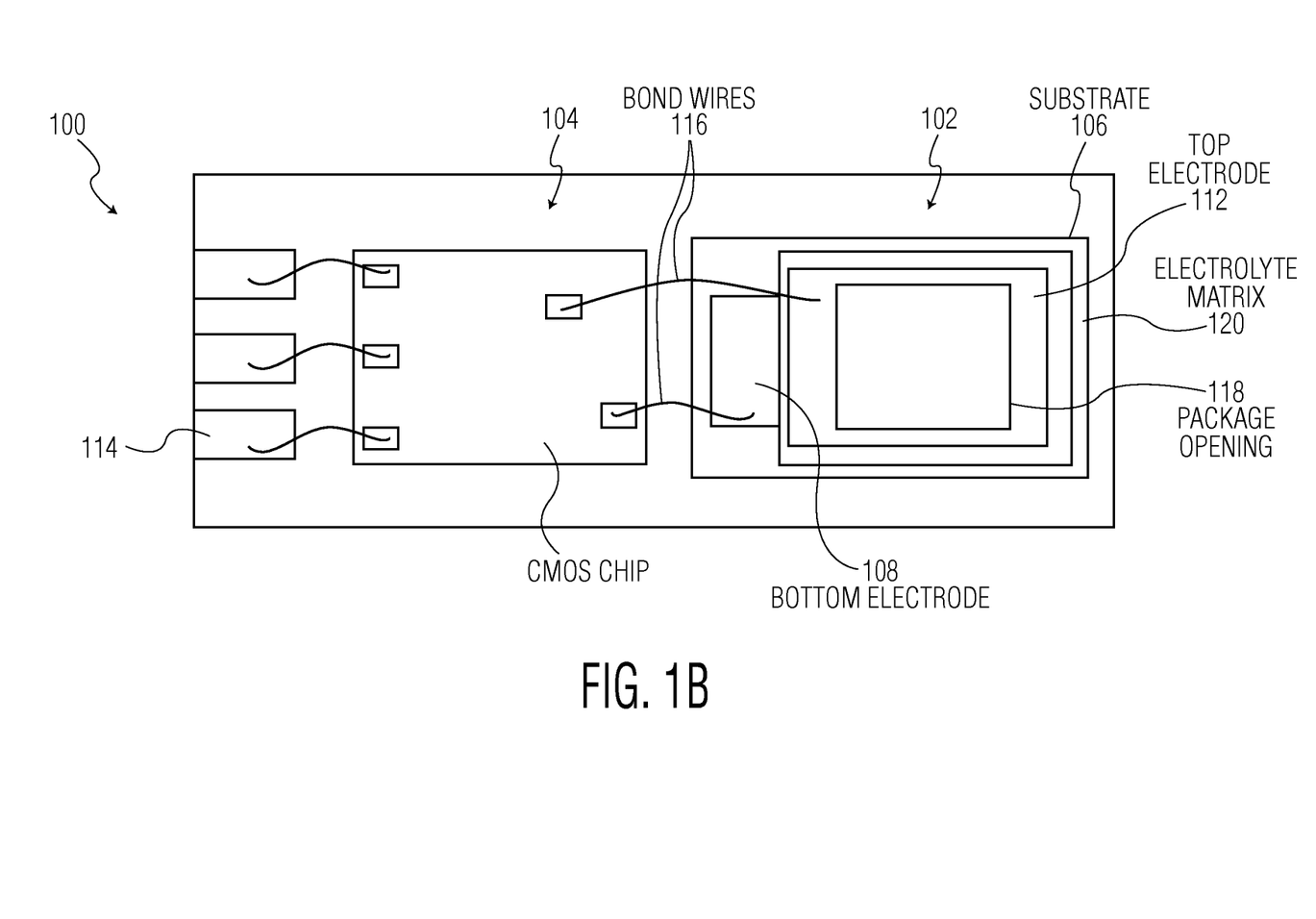

FIGS. 1A and 1B show one example of a first electrochemical sensor 100. The first electrochemical sensor 100 is in a three dimensional (3D) configuration with two electrode layers. An electrochemical cell is on a first die 102 and a potentiostat circuit with other read-out, buffering, data processing, memory and communications circuitry is on a second die 104.

The first die 102 includes a substrate 106. The substrate 106 can take many forms such that electrolyte which will later added to the first die 102 will not corrode or short circuit any other circuitry in the electrochemical sensor 100. Substrate 106 materials may include: a Si wafer with oxide or nitride layer; a glass plate; a polymer/plastic substrate, a water proof, chemically resistant adhesive compound.

A bottom electrode 108 is deposited and patterned on the substrate 106 perhaps using screen printing or lift-off techniques. The bottom electrode 108 in one example embodiment is a counter electrode, but in other embodiments could be either the working electrode or include an additional reference electrode.

A electrolyte matrix 110 is deposited and patterned on top of the bottom electrode 108. The electrolyte matrix 110 can be patterned with various techniques including: screen printing using polymers; inkjet printing using polymers or precursors for inorganic materials; blanket deposition and etch using a suitable mask needed; or sol gel deposition. The electrolyte matrix 110 could also be a fibrous substrate (e.g. of glass fiber meshwork which can contain and/or retain an electrolyte by capillary force). The electrolyte matrix 110 reposits (i.e. contains, stores up, includes, is a reservoir for, or soaks up) an electrolyte.

In one example, the electrolyte matrix 110 is a solid electrolyte structure or membrane, such as nafion. In other example embodiments, the electrolyte matrix 110 is a porous layer impregnated with a liquid electrolyte and the porous layer is made from: a porous inorganic material (e.g. Silicon Dioxide (SiO2), Aluminum Oxide (Al2O3), etc.); a porous organic material (e.g. polymer); or a non-porous inorganic material (e.g. SiO2 with 'pores' etched into the layer after deposition).

A top electrode 112 is deposited and patterned on the electrolyte matrix 110 perhaps using screen printing or lift-off techniques. The top electrode 112 in one example embodiment is a working electrode, but in other embodiments could be either the counter electrode or include an additional reference electrode.

The working, counter and reference electrodes in one example are made of platinum, alternatively the reference electrode is made from Ag/AgCl. Other electrode metals may be used depending on the gas to be sensed and the chemical reactions involved. The electrodes can serve as catalyst and be chemically stable to discourage corrosion. While FIGS. 1A and 1B show the top and bottom electrodes 112 and 108 as single electrodes, in other examples the bottom electrode 108 may be replaced with a separate counter electrode and reference electrode which are electrically isolated but are still patterned on the substrate 106. Also, to increase the electrochemical sensor's 100 sensitivity, one or both of the electrodes 112 and 108 may be arranged in special shapes (e.g. meanders or rings).

The potentiostat and other circuitry formed on the second die 104 is fabricated using standard CMOS techniques and connected to the first die 102 and a lead frame 114 with bond wires 116. The first and second dies 102 and 104 are then encapsulated 117 (e.g. over molded) leaving an opening 118 over the electrochemical sensor's top electrode 112 in the first die 102. The opening 118 permits the target gas to contact the top electrode 112 first during operation of the electrochemical sensor 100.

The electrolyte matrix 110 is then partially or completely filled with an electrolyte. If the electrolyte matrix 110 is a solid electrolyte, then additional electrolyte need not be added. The electrolyte can in one example reach the electrolyte matrix 110 through the opening 118 and a via (not shown) in the top electrode 112. In another example, the electrolyte reaches the electrolyte matrix 110 through a separate via provided elsewhere in the encapsulated sensor 100 package. The electrolyte can be applied by inkjet printing or micro drop which is gradually sucked up by the electrolyte matrix 110. The electrolyte matrix 110 with a liquid electrolyte is shown as 120 in FIG. 1A.

The electrolyte matrix 110 thus functions as a reservoir for storing the electrochemical sensor's 100 electrolyte. The electrolyte matrix 110 acts like a sponge by having open pores which suck up and store the electrolyte. Since the electrolyte matrix 110 acts like a scaffold for the electrolyte, the electrolyte matrix 110 keeps the top electrode 112 and bottom electrode 108 in a wetted condition irrespective of sensor orientation and environmental conditions (e.g. relative humidity) and thereby improves the electrochemical sensor's signal output stability and reduces the dependence of the sensor's signal output on environmental conditions.

The electrolyte matrix 110 also keeps the electrolyte layer thickness proximate to the electrodes at a constant level as the sensor's 100 orientation changes. In order to discourage evaporation of electrolyte, the electrolyte can be an ionic liquid having a very low vapor pressure and thus little or no evaporation.

During operation of one example of the first sensor 100 the working electrode is the top electrode 112 and is in first contact with the target gas mixture entering the opening 118. Depending on the type of gas (e.g. CO or VOC) to be detected and measured, the gas may be electrochemically oxidized or reduced at the working electrode. In this example, the bottom electrode 108 includes the counter electrode and optionally the reference electrode. In this example, the counter and reference electrodes are mostly screened from direct contact with the target gas to be sensed and are instead in contact with products from the electrochemical reaction of the gas mixture at the working electrode.

A distance which the target gas and reaction products molecules have to diffuse to each electrode differs. The distance to the top working electrode is much less than the distance to the bottom counter and reference electrodes, thereby creating a potential difference between top and bottom electrodes 112 and 108. The difference in distance causes the reaction products to reach the bottom electrode thus different species than the gas molecules on top electrodes. The difference in gas molecules at both electrodes causes the potential difference. This potential difference is the basis for a zero-bias electrical potentiostat circuit design to read-out the sensor. When the top electrode 112 is an anode, the oxidation of CO will no longer be transport controlled but will be reaction controlled. The local concentration ratio of $CO/O_2$ determines the local electrode potential $E_{mix}$.

While the following example embodiments are discussed with reference to a porous layer, these embodiments equally apply to embodiments where the porous layer is an electrolyte matrix.

Figure 2A:
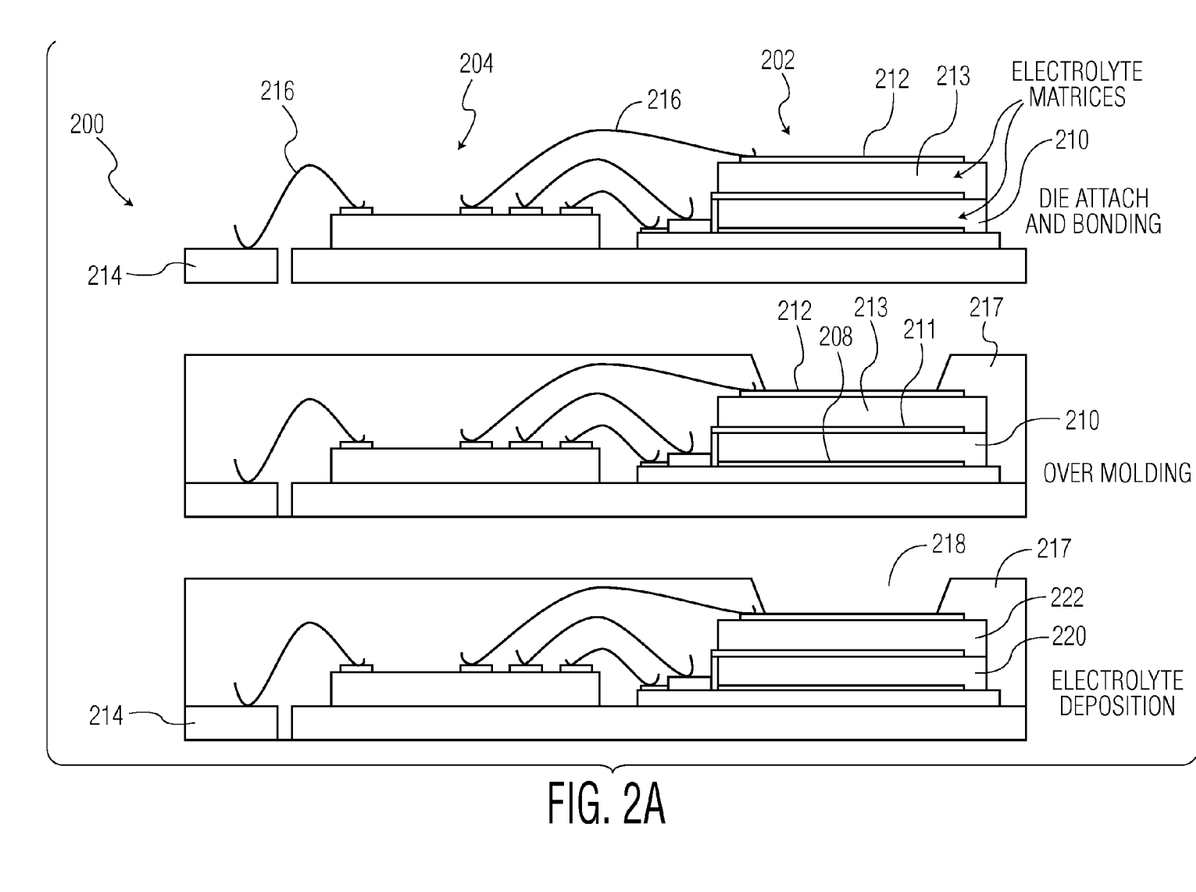
FIGS. 2A and 2B show one example of a second electrochemical sensor.
Figure 2B:
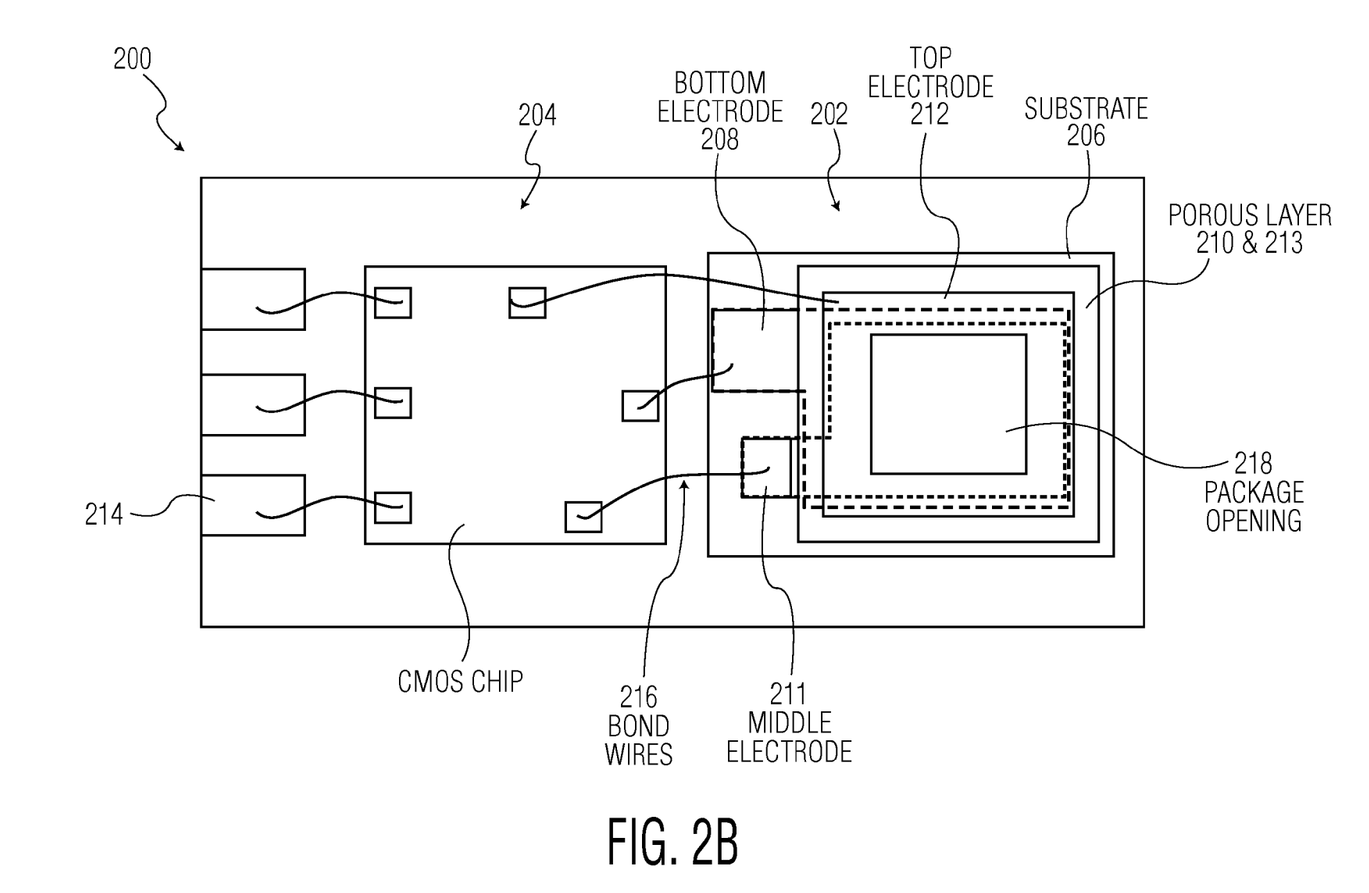

FIGS. 2A and 2B show one example of a second electrochemical sensor 200. This example embodiment of the second electrochemical sensor 200 shares similarities with the first electrochemical sensor 100 so mainly the differences between the first and second sensors 100 and 200 will be discussed. One difference is the instantiation of two porous layers between a bottom and top electrode, and the addition of a middle electrode between the two porous layers. In one example embodiment, the bottom electrode is a reference electrode, the middle electrode is a counter electrode, and the top electrode is a working electrode. Other example embodiments may have different top, middle and bottom electrode circuit functions.

An electrochemical cell is on a first die 202 and a potentiostat circuit with other read-out, buffering, data processing, memory and communications circuitry is on a second die 204.

The first die 202 includes an insulating substrate 206. A bottom electrode 208 is deposited and patterned on the substrate 206. The bottom electrode 208 in one example embodiment is a reference electrode, but in other embodiments could alternatively be either the working electrode or include an additional reference electrode.

A first porous layer 210 is deposited and patterned on top of the bottom electrode 208.

A middle electrode 211 is deposited and patterned on the first porous layer 210. The middle electrode 211 in one example embodiment is a counter electrode, but in other embodiments could be either the working electrode or reference electrode.

A second porous layer 213 is deposited and patterned on top of the middle electrode 211.

A top electrode 212 is deposited and patterned on the second porous layer 213. The top electrode 212 in one example embodiment is a working electrode, but in other embodiments could be either the counter electrode or the reference electrode.

While FIGS. 2A and 2B show the top, middle and bottom electrodes 212, 211 and 208 as single electrodes, in other examples the bottom electrode 208 may be replaced with multiple electrodes or arranged in special shapes (e.g. meanders or rings).

The potentiostat and other circuitry formed on the second die 204 is fabricated using standard CMOS techniques and connected to the first die 202 and a lead frame 214 with bond wires 216. The first and second dies 202 and 204 are then encapsulated 217 (e.g. over molded) leaving an opening 218 over the electrochemical sensor's top electrode 212 in the first die 202. The opening 218 permits the target gas to contact the top electrode 212 first during operation of the electrochemical sensor 200.

The first and second porous layers 210, 213 are then partially or completely filled with an electrolyte. The electrolyte can in one example reach the porous layers 210, 213 through the opening 218 and vias (not shown) in the top and middle electrodes 212, 211 (also if the layers are porous and the electrodes are thin the electrolyte can just go through the electrodes; no separate VIA is needed; in case of the embodiment with the separate reservoir the electrolyte can enter laterally/from the side). In another example, the electrolyte reaches the porous layers 210, 213 through separate vias provided elsewhere in the encapsulated sensor 200 package. The electrolyte can be applied by inkjet printing or micro drop which is gradually sucked up by the porous layers 210, 213. The first porous layer 210 with electrolyte is shown as 220 in FIG. 2A, and the second porous layer 213 with electrolyte is shown as 222.

Figure 3:
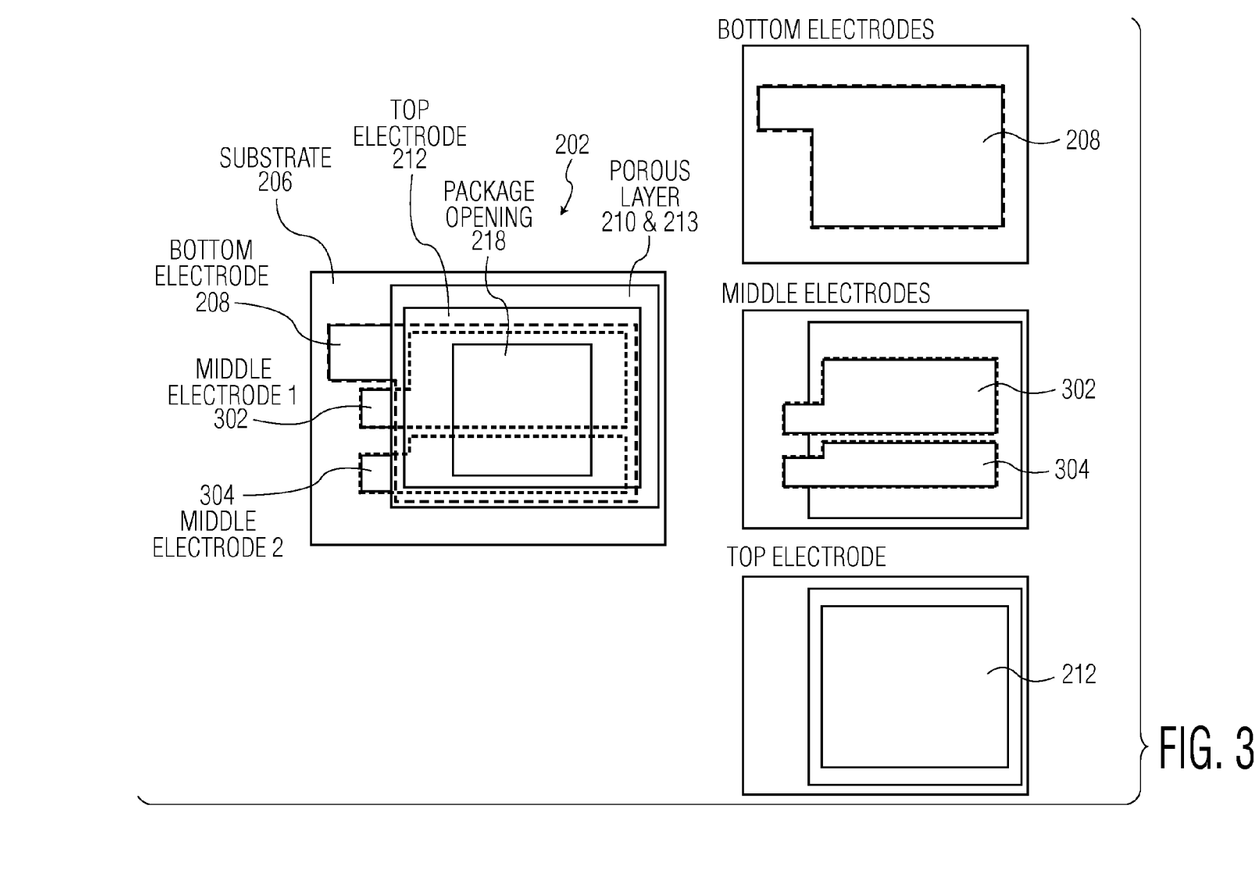
FIG. 3 shows one example of the second electrochemical sensor having two middle electrodes.

FIG. 3 shows one example of the second electrochemical sensor 200 having two middle electrodes. This second example embodiment of the second electrochemical sensor 200 shares similarities with the first example embodiment of the second electrochemical sensor 200. One difference is substitution of the single middle electrode 211 with a first middle electrode 302 and a second middle electrode 304. In one example embodiment, the bottom electrode 208 is a first reference electrode, the first middle electrode 302 is a counter electrode, the second middle electrode 304 is a second reference electrode, and the top electrode 212 is a working electrode. Example embodiments having these two reference electrodes can enable a higher accuracy electrochemical cell intended for detection of trace target gases at very low concentration.

Other example embodiments may have different top, first middle, second middle and bottom electrode circuit functions.

Figure 4A:
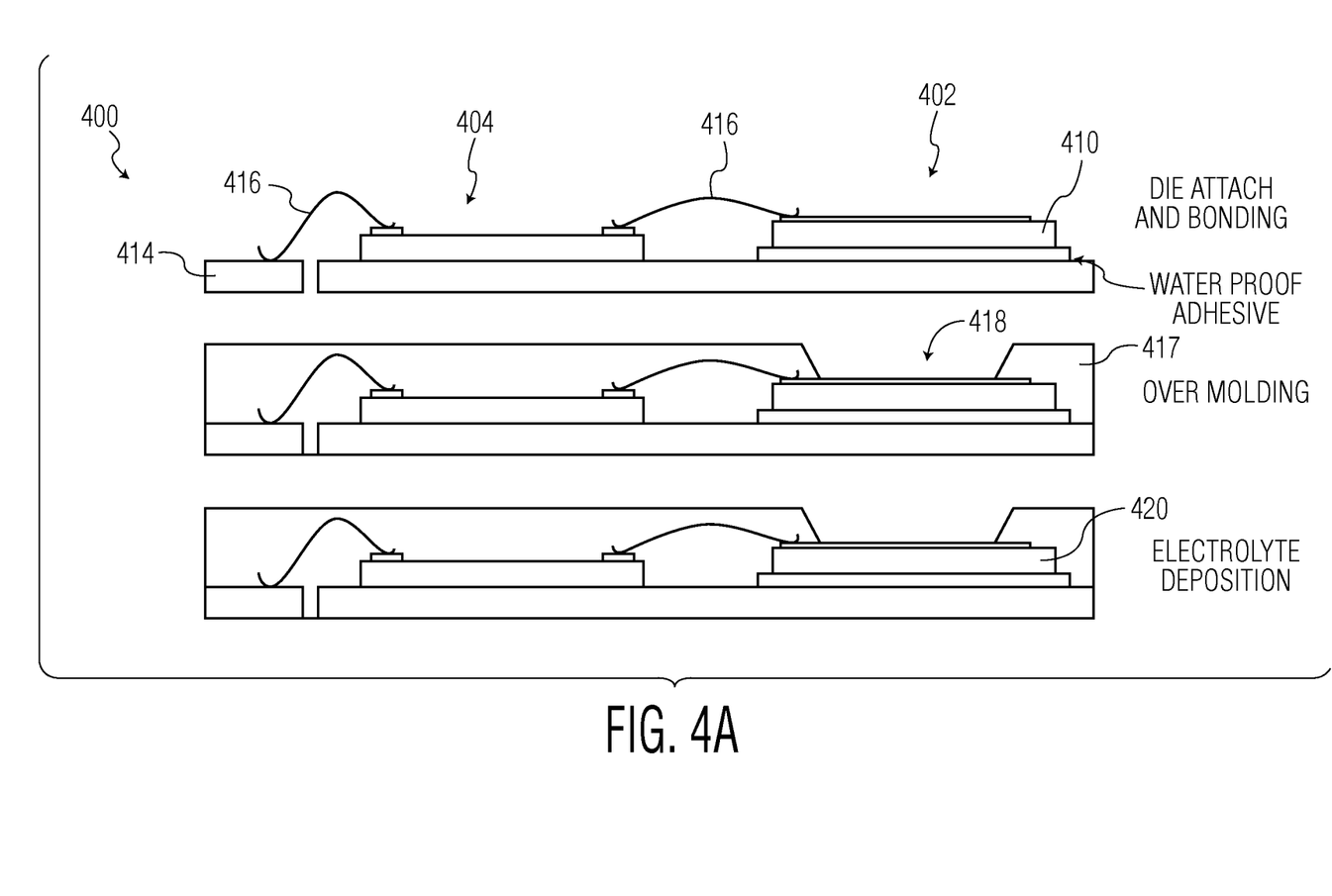
FIGS. 4A and 4B show one example of a third electrochemical sensor.
Figure 4B:
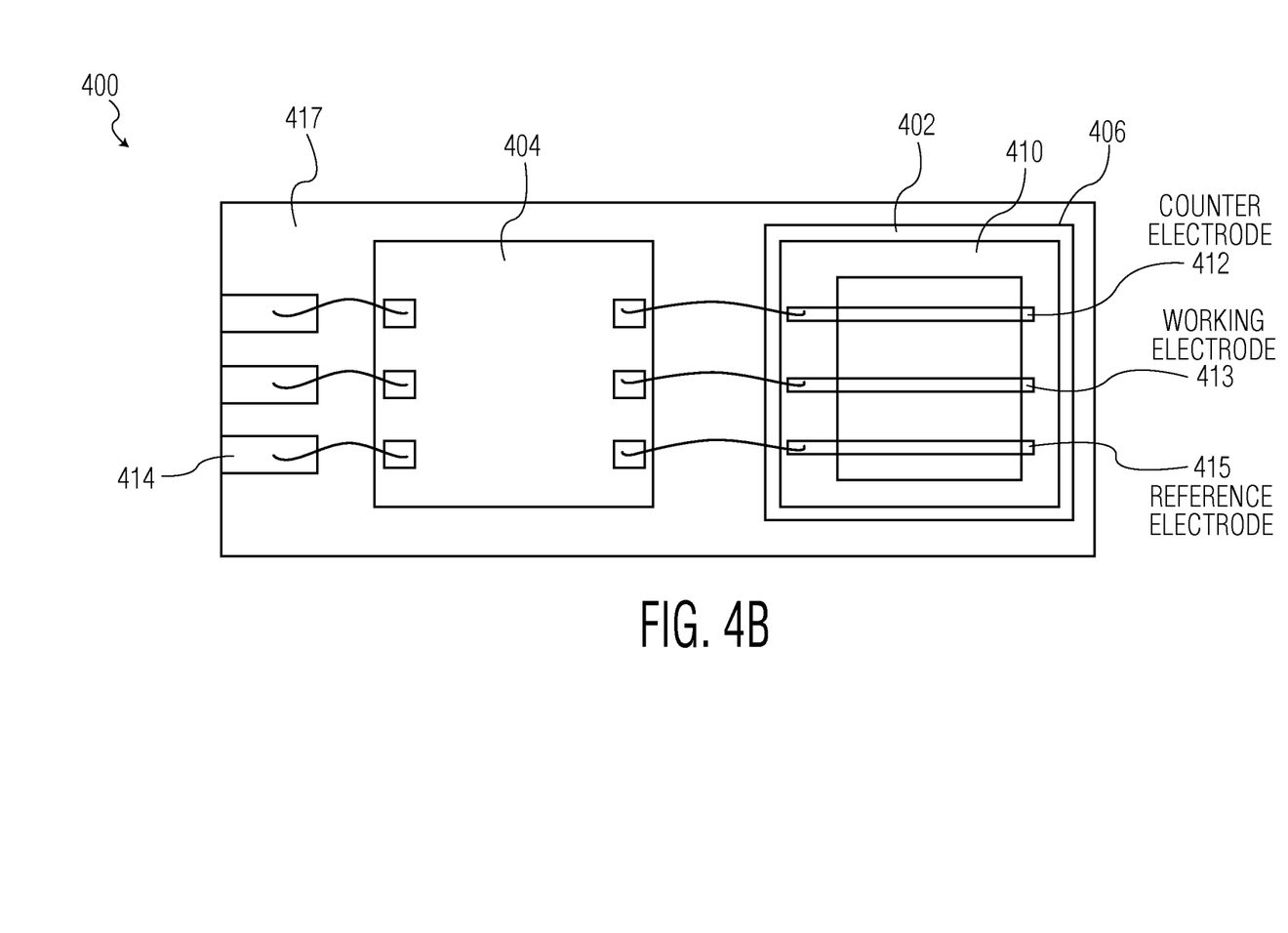

FIGS. 4A and 4B show one example of a third electrochemical sensor 400. The third electrochemical sensor 400 is in a two dimensional (2D) configuration with one electrode layer. An electrochemical cell is on a first die 402 and a potentiostat circuit with other read-out, buffering, data processing, memory and communications circuitry is on a second die 404.

The first die 402 includes an insulating substrate 406. A porous layer 410 is deposited and patterned on top of the substrate 406. A first, second and third top electrode 412, 413, 415 are deposited and patterned on the porous layer 410. In one example embodiment the first top electrode 412 is a counter electrode, the second top electrode 413 is a working electrode, and the third top electrode 415 is a reference electrode. In other embodiments these top electrodes 412, 413, 415 could be assigned other functions or only two electrodes 412, 413 could be used.

The potentiostat and other circuitry formed on the second die 404 is fabricated using standard CMOS techniques and connected to the first die 402 and a lead frame 414 with bond wires 416. The first and second dies 402 and 404 are then encapsulated 417 (e.g. over molded) leaving an opening 418 over the electrochemical sensor's top electrode 412 in the first die 402. The opening 418 permits the target gas to contact the top electrodes 412, 413, 415 during operation of the electrochemical sensor 400.

The porous layer 410 is then partially or completely filled with an electrolyte. The electrolyte can in one example reach the porous layer 410 through the opening 418 in the top electrode 412. In another example, the electrolyte reaches the porous layer 410 through a separate via provided elsewhere in the encapsulated sensor 400 package. The porous layer 410 with electrolyte is shown as 420 in FIG. 4A.

In this 2D electrode configuration, the electrodes are in a planar arrangement and all electrodes are exposed to the same gases through the opening 418. A potential difference is applied between the electrodes to drive the reaction. With the electrodes on top, the sensor 400 current is not restricted by the electrolyte layer thickness and diffusion processes is governed by the much higher reaction rates for the reaction at the electrodes. In an alternate example embodiment (not shown), electrodes 412, 413, 415 are instead placed on the substrate 406 underneath the porous layer 410 and the target gas molecules must diffuse through the porous layer with electrolyte 420 before reacting at the electrodes 412, 413, 415.

Figure 5:
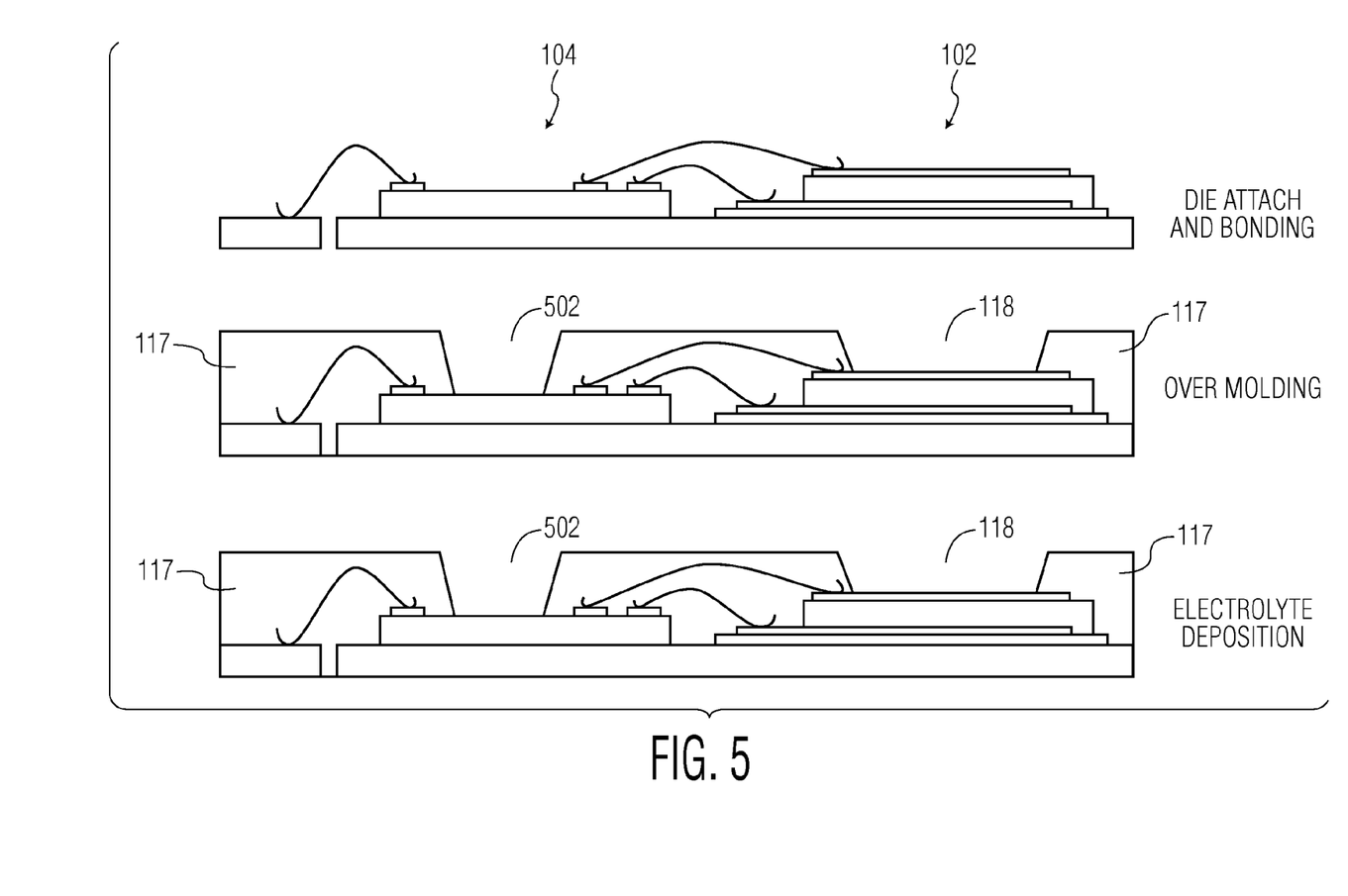
FIG. 5 shows one example of the first electrochemical sensor having an additional sensor.

FIG. 5 shows one example of the first electrochemical sensor 100 having an additional sensor. As discussed for the first electrochemical sensor 100, the second die 102 includes the potentiostat and other circuitry; however, in this example embodiment, the second die 102 further includes additional sensing functionality such as a temperature sensor, a relative humidity sensor and/or other environmental sensors. The first and second dies 102 and 104 are then encapsulated 117 (e.g. over molded) leaving the opening 118 over the electrochemical sensor's top electrode 112 in the first die 102, but also leaving a second opening 502 over the additional sensing functionality in the second die 104. These openings 118, 502 permit various elements and/or molecules to interact with the electrochemical cell in the first die 102 and the additional sensing functionality in the second die 104 during operation of the electrochemical sensor 100. The additional sensing functionality can be used to compensate for potential cross sensitivities of the electrochemical cell. Electrochemical cell may be sensitive e.g. to also relative humidity and temperature. In order to compensate for this effect a separate relative humidity sensor can be added.

Figure 6:
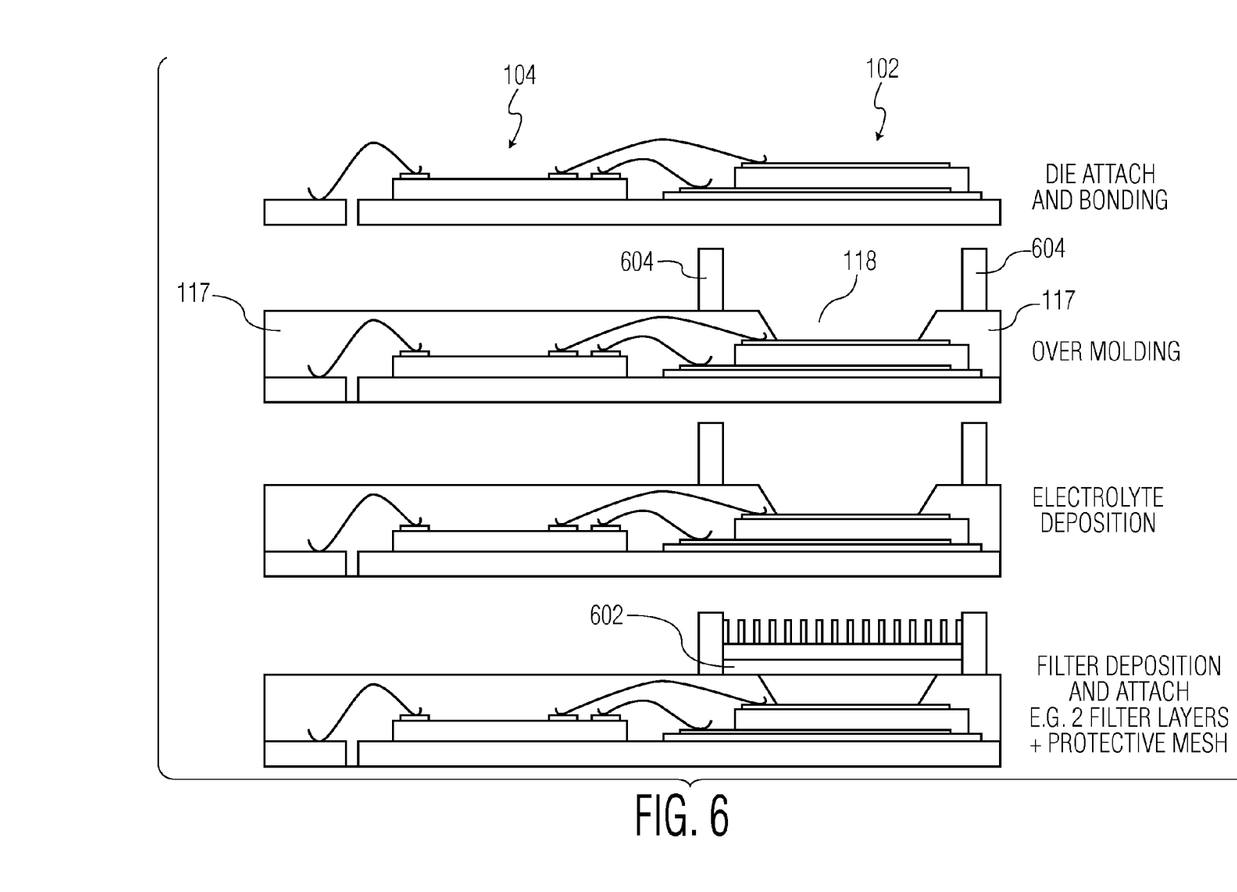
FIG. 6 shows one example of the first electrochemical sensor having a filter.

FIG. 6 shows one example of the first electrochemical sensor 100 having a filter 602. The filter 602 is placed over the opening 118 which is above the electrochemical cell in the first die 102. In one example embodiment the filter 602 improves the electrochemical sensor's 100 target chemical selectivity by blocking one or more non-target substances (e.g. a CO sensor could include a filter to oxidize ethanol vapors which could cause similar electrode currents as the CO to be detected).

The filter 602 is fixed above the opening 118 with anchoring structures 604 (e.g. pins, rings, adhesives). The anchoring structures 604 can be directly formed by and/or integrated into the encapsulation 117. Individual filter 602 layers can be cut with a punch tool, applied by a pick and place machine, and glued or ultrasonically welded to the anchoring structures 604. The filter 602 may also serve to protect the electrochemical cell in the first die 102 from contaminants and reduce evaporation of the electrolyte from the electrolyte matrix 110. A filter 602 which minimizes evaporation includes a semi permeable membrane that allows passage of e.g. CO but not $H_2O$.

Figure 7:
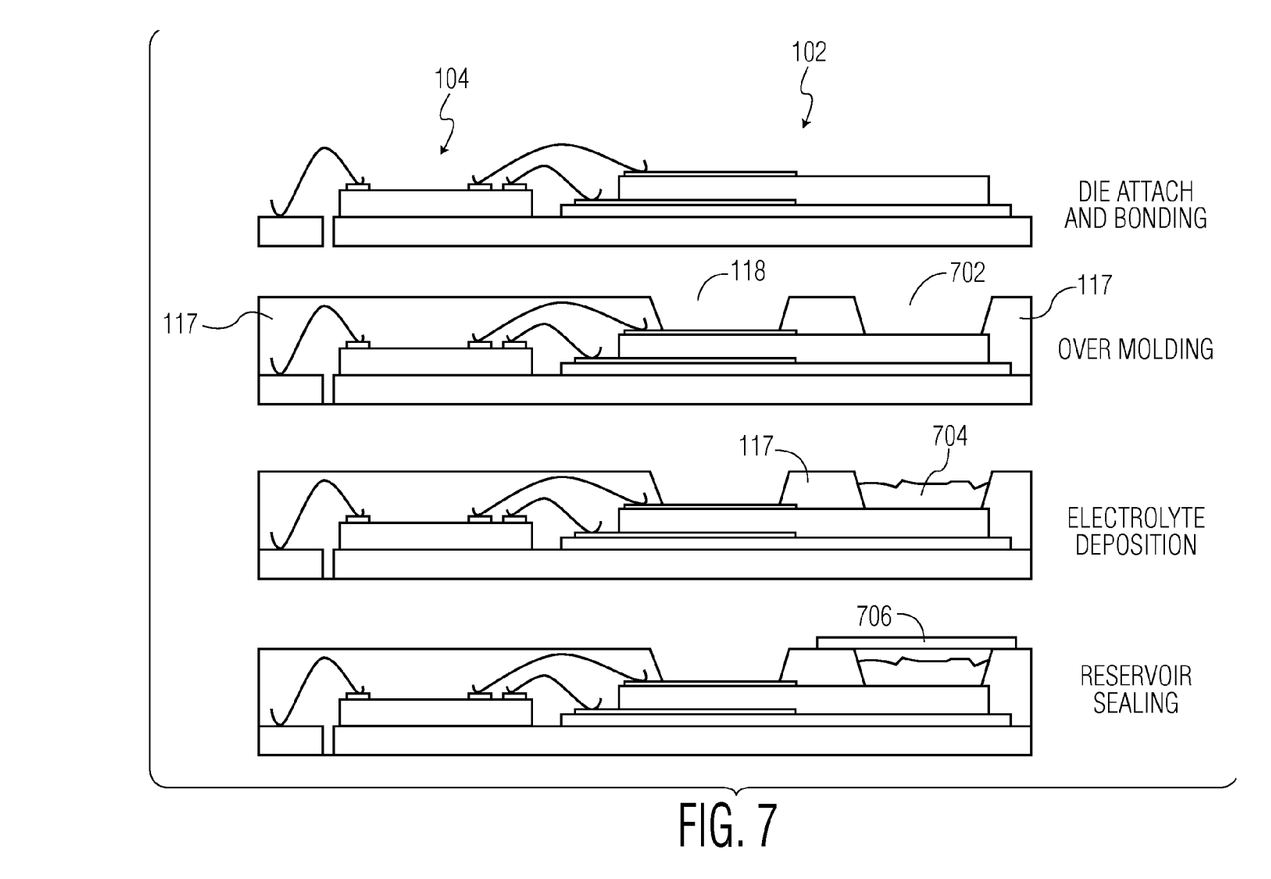
FIG. 7 shows one example of the first electrochemical sensor having a reservoir.

FIG. 7 shows one example of the first electrochemical sensor 100 having a reservoir. This example embodiment is similar to the embodiment shown in FIGS. 1A and 1B except that, in the first die 102, the substrate 106 and the electrolyte matrix 110 have be extended in a lateral direction while the top and bottom electrodes 112, 108 have retained their previous lateral dimensions.

The first and second dies 102 and 104 are then encapsulated 117 leaving the opening 118 over the electrochemical sensor's top electrode 112 and adding a second opening 702 over the electrolyte matrix 110. The electrolyte matrix 110 is then partially or completely filled with an electrolyte 704. The electrolyte 704 is also is added into the second opening 702, thereby forming a reservoir of the electrolyte 704. This reservoir of electrolyte further buffers potential evaporation or uptake of water by the electrolyte matrix 110. A cover 706 can be added over the second opening 702 to further counteract any effects of evaporation on the electrolyte 704 in the reservoir.

Figure 8:
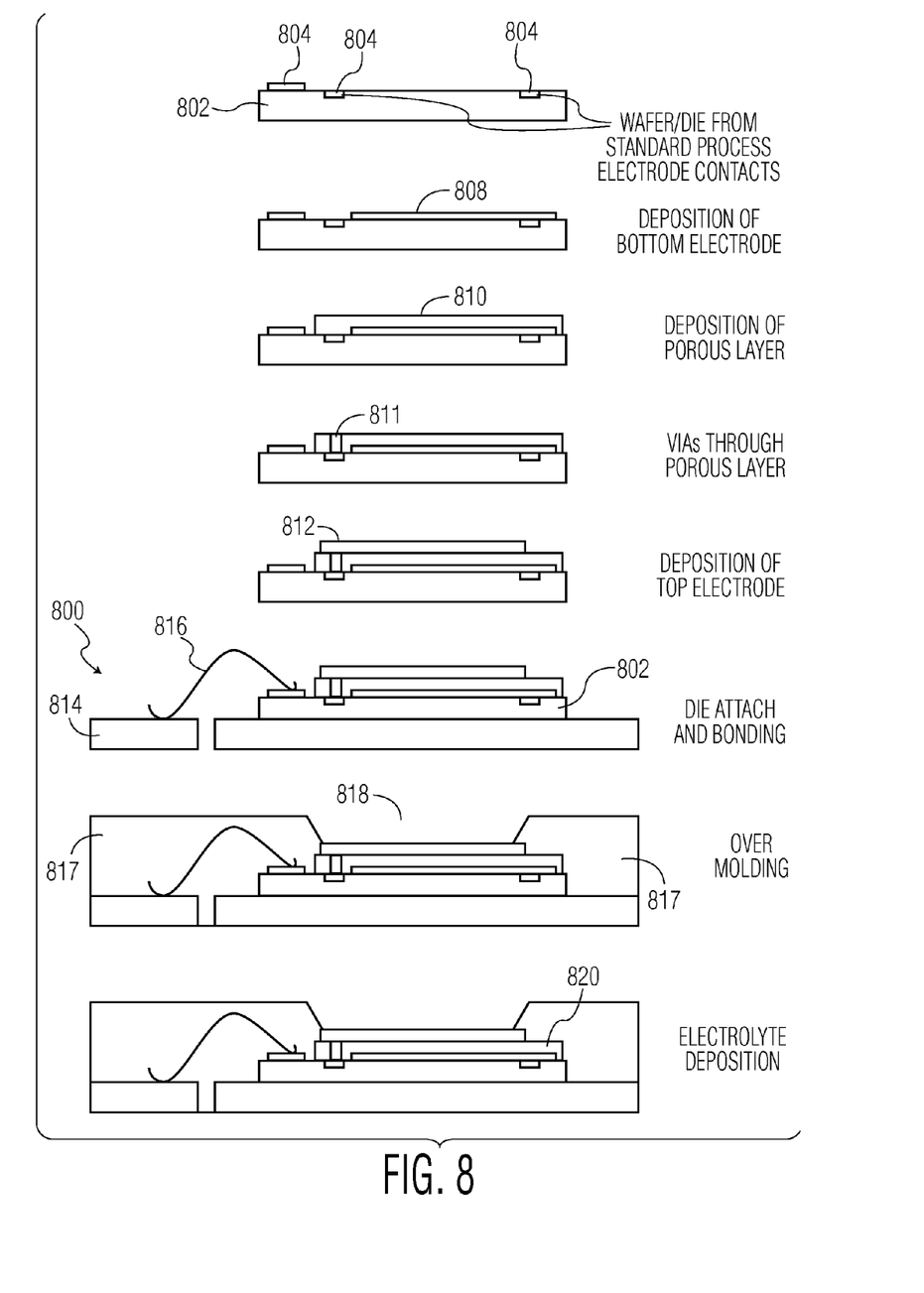
FIG. 8 shows one example of the first electrochemical sensor having a stacked configuration.

FIG. 8 shows one example of a fourth electrochemical sensor 800 having a stacked configuration. The fourth electrochemical sensor 800 is in a three dimensional (3D) configuration with two electrode layers. An electronic circuit with potentiostat, read-out, buffering, data processing, memory and communications circuitry, and an electrochemical cell are stacked together within a die 802.

The die 802 includes a planarized passivation stack (not shown) on top. The passivation stack serves as barrier layer from an electrolyte filled porous layer within the electrochemical cell on top of the die 802. Additional layers (e.g. metal, platinum, silicon nitride) can be deposited on top of this passivation stack to augment the barrier layer.

The die 802 includes the electronic circuit for the potentiostat and other electronics onto which a set of output electrodes 804 are patterned. A bottom electrode 808 is deposited and patterned on the die 802 and in contact with one of the set of output electrodes 804. The bottom electrode 808 in one example embodiment is a counter electrode, but in other embodiments could be either the working electrode or a reference electrode.

A porous layer 810 is deposited and patterned on top of the bottom electrode 808 and in contact with another one of the set of output electrodes 804. A via 811 (e.g. tungsten, preferably same material as top electrode otherwise risk of electrochemical reactions/corrosion) is created through the porous layer 810 and is electrically connected to another one of the set of output electrodes 804.

A top electrode 812 is deposited and patterned on the porous layer 810 and in electrical contact with the via 811. The top electrode 812 in one example embodiment is a working electrode, but in other embodiments could be either a counter electrode or a reference electrode.

The die 802 is connected to a lead frame 814 with bond wires 816. The die 802 is then encapsulated 817 (e.g. over molded) leaving an opening 818 over the electrochemical sensor's top electrode 812 in the die 802. The opening 818 permits the target gas to contact the top electrode 812 first during operation of the electrochemical sensor 800.

The porous layer 810 is then partially or completely filled with an electrolyte. The electrolyte can in one example reach the porous layer 810 through the opening 818 and a via (not shown) in the top electrode 812. In another example, the electrolyte reaches the porous layer 810 through a separate via provided elsewhere in the encapsulated sensor 800 package. The porous layer 810 with electrolyte is shown as 820 in FIG. 8. However, the porous layer can be porous enough so that the liquid electrolyte will penetrate through the electrode material film.

In an alternate example, the via 811 can be omitted by connecting the top electrode 812 to the lead frame 814 with a separate bond wire 816.

Figure 9:
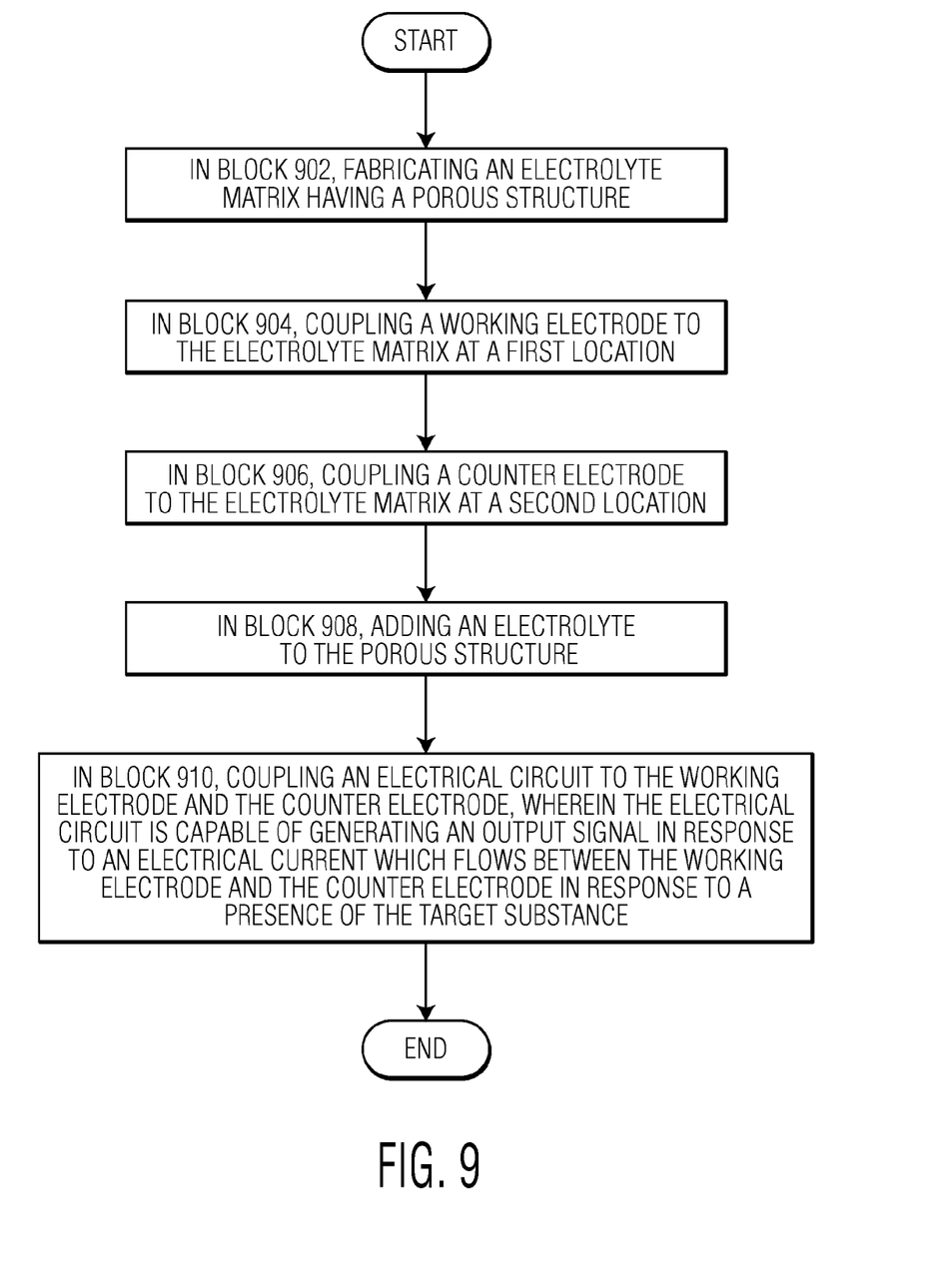
FIG. 9 is a first example of a method for manufacturing an electrochemical sensor.

FIG. 9 is a first example of a method 900 for manufacturing an electrochemical sensor for sensing a target substance. The method 900 begins in block 902, by fabricating a electrolyte matrix having a porous structure. Next, in block 904, coupling a working electrode to the electrolyte matrix at a first location is performed. In block 906, coupling a counter electrode to the electrolyte matrix at a second location occurs. In block 908 an electrolyte is added to the porous structure. Then in block 910, an electrical circuit is coupled to the working electrode and the counter electrode, wherein the electrical circuit is capable of generating an output signal in response to an electrical current which flows between the working electrode and the counter electrode in response to a presence of the target substance. While the order in which these steps are implemented can be changed, the proposed sequence aims at manufacturing electrochemical cell first independently before connecting to read out electronics. Alternately steps 908 and 910 can be switched during wafer processing.

The blocks comprising the flowcharts in the above Figures can be effected in any order, unless a specific order is explicitly stated. Also, those skilled in the art will recognize that while one example method embodiment is now discussed, the material in this specification can be combined in a variety of ways to yield other examples as well. The method next discussed is to be understood within a context provided by this and other portions of this detailed description.

Example embodiments of the material discussed in this specification can be implemented in whole or in part through network, computer, or data based devices and/or services. These may include cloud, internet, intranet, mobile, desktop, processor, look-up table, microcontroller, consumer equipment, infrastructure, or other enabling devices and services. As may be used herein and in the claims, the following non-exclusive definitions are provided.

In some example embodiments the method steps described above are implemented as functional and software instructions embodied as a set of executable instructions which are effected on a computer which is programmed with and controlled by said executable instructions. Such instructions are loaded for execution on a processor (such as one or more CPUs). The processor includes microprocessors, microcontrollers, processor modules or subsystems (including one or more microprocessors or microcontrollers), or other control or computing devices. A processor can refer to a single component or to plural components.

In one example, one or more blocks or steps discussed herein are automated. In other words, apparatus, systems, and methods occur automatically. The terms automated or automatically (and like variations thereof) mean controlled operation of an apparatus, system, and/or process using computers and/or mechanical/electrical devices without the necessity of human intervention, observation, effort and/or decision.

In some examples, the methods illustrated herein and data and instructions associated therewith are stored in respective storage devices, which are implemented as one or more non-transient computer-readable or computer-usable storage media or mediums. The non-transient computer-usable media or mediums as defined herein excludes signals, but such media or mediums may be capable of receiving and processing information from signals and/or other transient mediums. The storage media include different forms of memory including semiconductor memory devices such as DRAM, or SRAM, Erasable and Programmable Read-Only Memories (EPROMs), Electrically Erasable and Programmable Read-Only Memories (EEPROMs) and flash memories; magnetic disks such as fixed, floppy and removable disks; other magnetic media including tape; and optical media such as Compact Disks (CDs) or Digital Versatile Disks (DVDs). Note that the instructions of the software discussed above can be provided on one computer-readable or computer-usable storage medium, or alternatively, can be provided on multiple computer-readable or computer-usable storage media distributed in a large system having possibly plural nodes. Such computer-readable or computer-usable storage medium or media is (are) considered to be part of an article (or article of manufacture). An article or article of manufacture can refer to any manufactured single component or multiple components.

In this specification, example embodiments have been presented in terms of a selected set of details. However, a person of ordinary skill in the art would understand that many other example embodiments may be practiced which include a different selected set of these details. It is intended that the following claims cover all possible example embodiments.

What is claimed is:

1. An electrochemical sensor for sensing a target substance, comprising:
    an electrochemical cell including an electrolyte matrix, wherein the matrix reposits an electrolyte;
    a working electrode coupled to the electrolyte matrix at a first location;
    a counter electrode coupled to the electrolyte matrix at a second location; and
    an electrical circuit which includes a potentiostat, is coupled to the working electrode and the counter electrode, and is capable of generating an output signal in response to an electrical current which flows between the working electrode and the counter electrode in response to a presence of the target substance,
    wherein the electrochemical cell and the potentiostat are co-integrated within a substrate, and
    wherein the substrate is located on a first side of the potentiostat and the electrochemical cell is located on a side opposite to the first side of the potentiostat.

2. The sensor of claim 1, wherein the electrolyte matrix is one from a group consisting of:
    a solid electrolyte and nafion.

3. The sensor of claim 1, wherein the electrolyte matrix is a porous layer impregnated with a liquid electrolyte, and
    wherein the porous layer includes at least one from a group consisting of: a porous inorganic material, Silicon Dioxide, Aluminum Oxide, a porous organic material, a polymer, a non-porous inorganic material having pores, a fibrous substrate, and a glass fiber meshwork.

4. The sensor of claim 1, wherein the electrolyte matrix keeps the electrodes in contact with the electrolyte irrespective of the electrochemical sensor's physical orientation.

5. The sensor of claim 1, wherein the potentiostat is coupled to the working and counter electrodes.

6. The sensor of claim 1, wherein the working electrode is located between the target substance and a first side of the electrolyte matrix, and the counter electrode is located between the substrate and a side opposite to the first side of the electrolyte matrix.

7. The sensor of claim 1, wherein the working electrode and the counter electrode are located between the target substance and a first side of the electrolyte matrix.

8. The sensor of claim 1, wherein the target substance contacts the working electrode before contacting the counter electrode.

9. The sensor of claim 1, wherein the target substance is at least one from a group consisting of: a gas, a liquid, a solid, a molecule, a chemical element, and a carbon compound.

10. The sensor of claim 1, wherein the substrate includes at least one from a group consisting of: silicon, silicon dioxide, nitride layer; glass; a polymer, a water proof compound, a chemically resistant compound.

11. The sensor of claim 1, further comprising:
an encapsulation enclosing the electrical circuit and having an opening,
wherein the opening is positioned above the electrochemical cell, and
wherein the encapsulation includes a second opening positioned above an environmental sensor in the electrical circuit.

12. The sensor of claim 1, further comprising an electrolyte reservoir proximate to the electrolyte matrix and replenishing the electrolyte in the electrolyte matrix.

13. The sensor of claim 1, wherein the electrochemical cell and the potentiostat are fabricated using CMOS processes.

14. An electrochemical sensor for sensing a target substance, comprising:
an electrochemical cell including an electrolyte matrix, wherein the matrix reposits an electrolyte;
a working electrode coupled to the electrolyte matrix at a first location; and a counter electrode coupled to the electrolyte matrix at a second location;
an electrical circuit, coupled to the working electrode and the counter electrode, and capable of generating an output signal in response to an electrical current which flows between the working electrode and the counter electrode in response to a presence of the target substance; and
an encapsulation enclosing the electrical circuit and having an opening,
wherein the opening is positioned above the electrochemical cell, and
wherein the encapsulation includes a second opening positioned above an environmental sensor in the electrical circuit.

15. The sensor of claim 14, further comprising a filter proximate to the opening and blocking one or more non-target substances.

16. A method for manufacturing an electrochemical sensor for sensing a target substance, comprising:
fabricating a electrolyte matrix, wherein the matrix reposits an electrolyte, and wherein the electrolyte matrix is included in an electrochemical cell;
coupling a working electrode to the electrolyte matrix at a first location;
coupling a counter electrode to the electrolyte matrix at a second location;
and
coupling an electrical circuit which includes a potentiostat to the working electrode and the counter electrode, wherein the electrical circuit is capable of generating an output signal in response to an electrical current which flows between the working electrode and the counter electrode in response to a presence of the target substance,
wherein the electrochemical cell and the potentiostat are co-integrated within a substrate, and
wherein the substrate is located on a first side of the potentiostat and the electrochemical cell is located on a side opposite to the first side of the potentiostat.

* * * * *